(12) United States Patent
Andrews et al.

(10) Patent No.: US 6,210,315 B1
(45) Date of Patent: Apr. 3, 2001

(54) BRACHYTHERAPY DEVICE INCLUDING AN ANTI-STATIC HANDLE

(75) Inventors: Marvin O. Andrews; Frank J. Fischer, Jr., both of Bloomington; John H. Ward, Spencer, all of IN (US)

(73) Assignee: Cook Urological Inc., Spencer, IN (US)

( * ) Notice: Subject to any disclaimer, the term of this patent is extended or adjusted under 35 U.S.C. 154(b) by 0 days.

(21) Appl. No.: 09/354,073

(22) Filed: Jul. 15, 1999

Related U.S. Application Data

(60) Provisional application No. 60/093,469, filed on Jul. 20, 1998.

(51) Int. Cl.$^7$ .................................................. A61N 5/00
(52) U.S. Cl. ..................................... 600/7; 600/3; 604/57
(58) Field of Search .................................. 600/7, 8, 3, 1; 604/57, 60

(56) References Cited

U.S. PATENT DOCUMENTS

| | | |
|---|---|---|
| 3,070,132 | 12/1962 | Sheridan . |
| 3,914,002 | 10/1975 | Berliner et al. . |
| 4,086,914 | 5/1978 | Moore . |
| 4,402,308 | 9/1983 | Scott . |
| 4,627,420 * | 12/1986 | Katz ........................... 600/7 |
| 5,141,487 | 8/1992 | Liprie . |
| 5,242,373 | 9/1993 | Scott et al. . |
| 5,380,290 | 1/1995 | Makower et al. . |
| 5,484,284 | 1/1996 | Fearnot . |
| 5,860,909 * | 1/1999 | Mick et al. ................. 600/7 |
| 5,928,130 * | 7/1999 | Schmidt ..................... 600/7 |
| 5,938,583 * | 8/1999 | Grimm ....................... 600/7 |
| 6,007,474 * | 12/1999 | Rydell ........................ 600/7 |
| 6,095,967 * | 8/2000 | Black et al. ................ 600/7 |
| 6,102,844 * | 8/2000 | Ravins et al. .............. 600/7 |

FOREIGN PATENT DOCUMENTS 4109205  9/1992  (DE) .

* cited by examiner

Primary Examiner—Cary O'Connor
Assistant Examiner—Navin Natnithithadha
(74) Attorney, Agent, or Firm—Richard J. Godlewski; James B. Hunt

(57) ABSTRACT

A brachytherapy device 10 for exposing to radioactivity a patient includes an elongate member such as a needle or cannula 12 adapted for introduction into the patient and also includes a stylet 14 slideably receivable in a longitudinal throughbore 16 in the needle 12. The device 10 also includes a portion 64 near either the proximal end 18 of the needle 12 or the distal end 24 of the stylet 14 which provides a local, defined amount of friction between the needle 12 and the stylet 14. The device 10 further includes an anti-static handle 34 connected to the needle 12. The handle 34 has an interior ramp surface 40 in communication with the throughbore 16 of the needle 12, frustoconical in shape and possessing an included apical angle of at least about 16°. The localized friction portion 64 can be a crimp or flange 48 on the stylet 14, or a crimp 44 or deformation 46 in or of the needle 12. The handle 34 is preferably composed of a polycarbonate, acrylic or acetal resin (such resins preferably being carbon-filled, or otherwise electro static dissipative), or a hydroscopic nylon blend. The device 10 is particularly advantageous in that the preferred ramp surface 40 in the handle 34 facilitates the insertion of seeds 26 of radioactive material and inert spacers 28 into the needle 12. The anti-static handle 34 eliminates, for practical purposes, the previously encountered risks of static interference, static cling of the spacers 28 and ignition spark generation. Finally, the localized friction portion 64 provides a controlled and predetermined amount of friction between the needle 12 and the stylet 14, preventing the stylet 14 from falling from the needle 12, while also preventing or reducing the risk of unintended ejection of the radioactive seeds 26 and spacers 28. Such friction is advantageously provided virtually the entire time any portion of the stylet 14 is received in the needle 12.

20 Claims, 4 Drawing Sheets

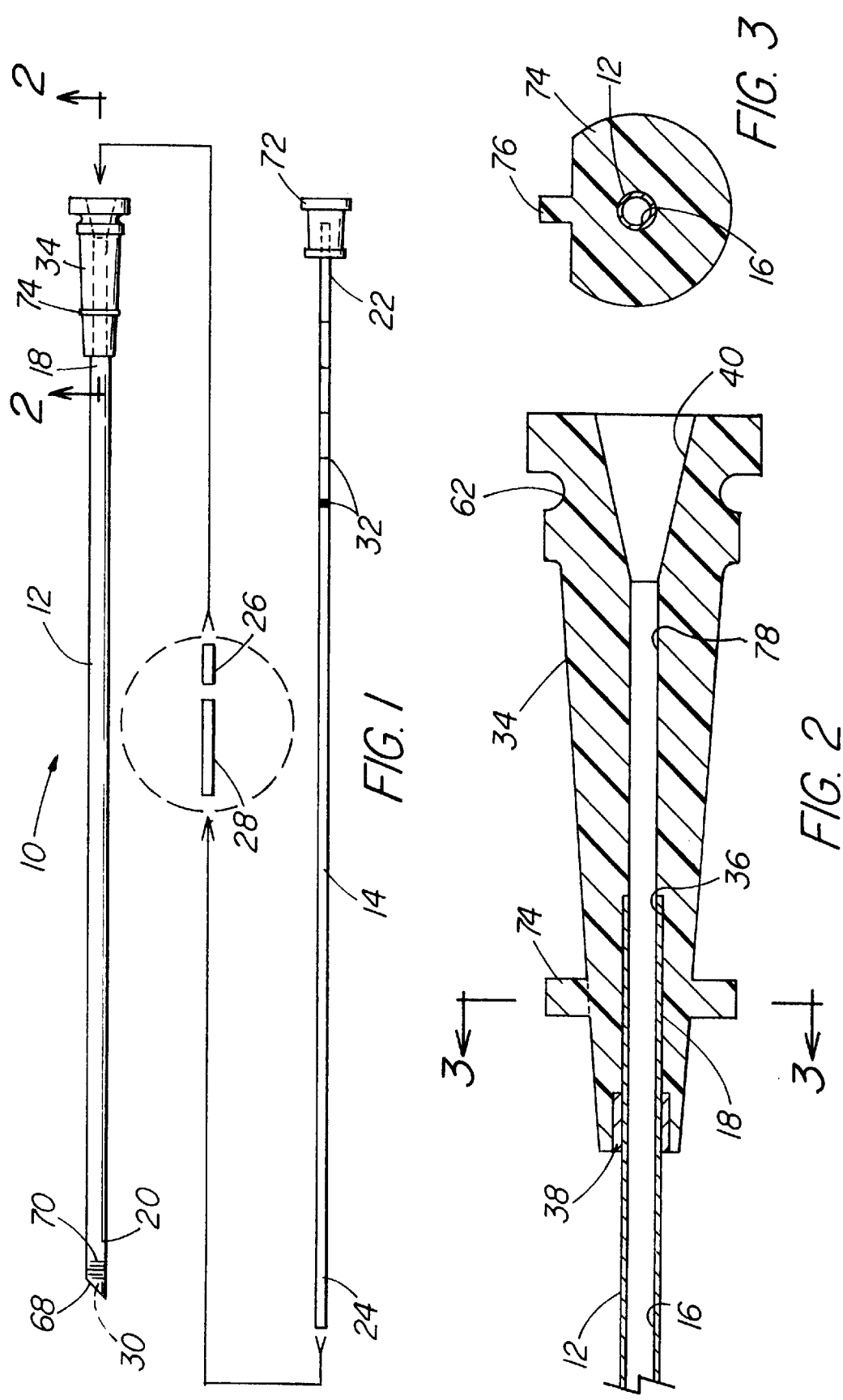

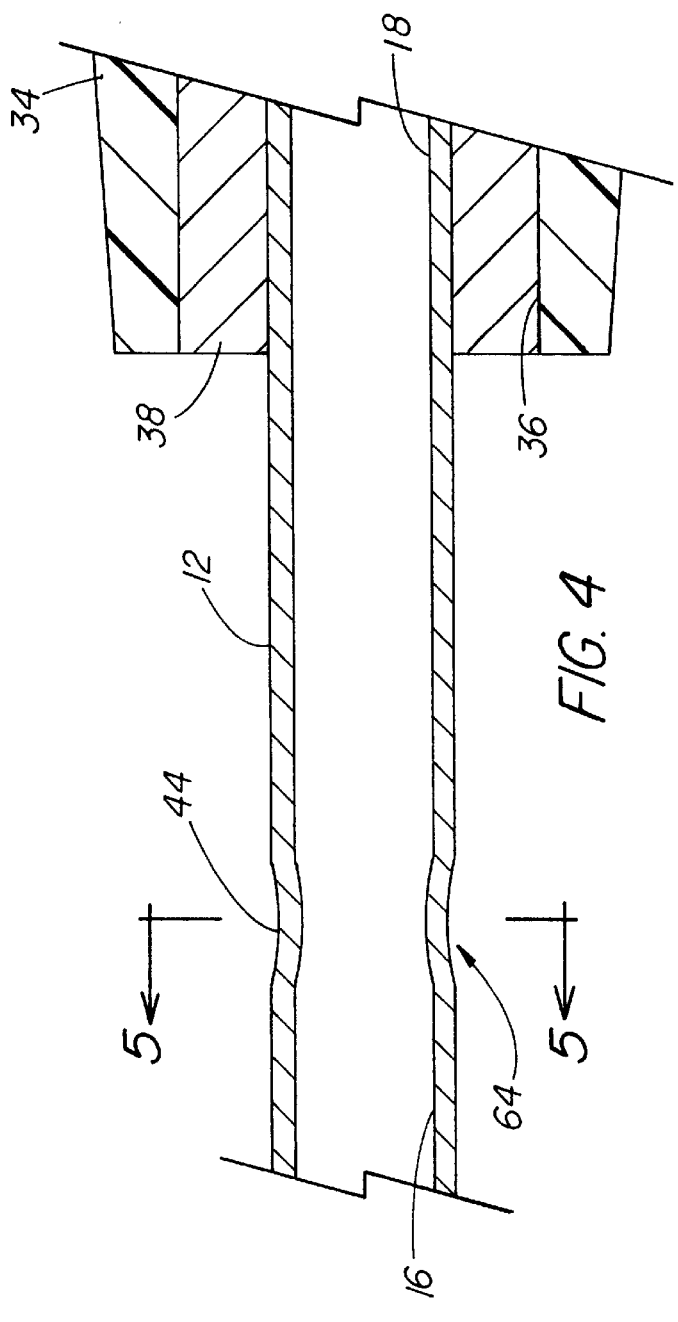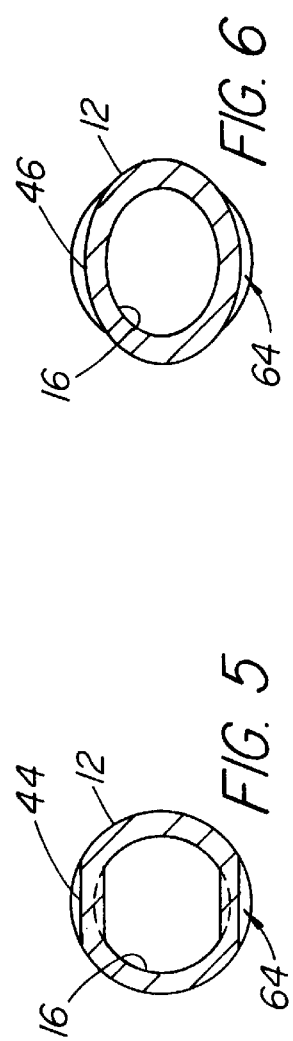

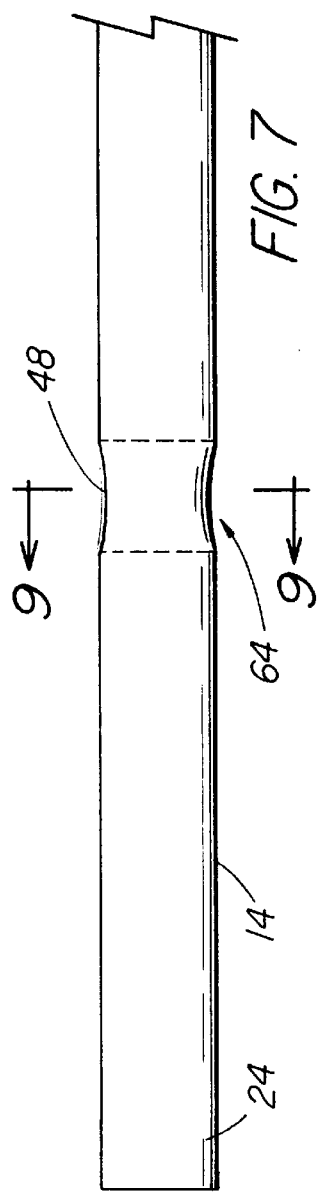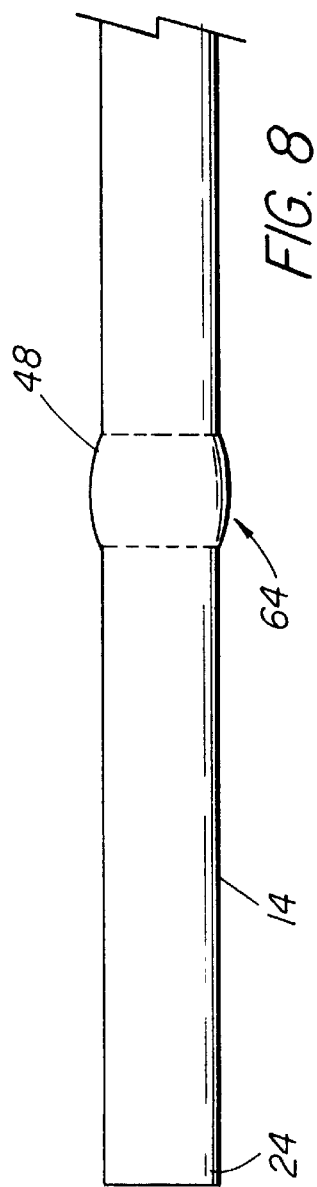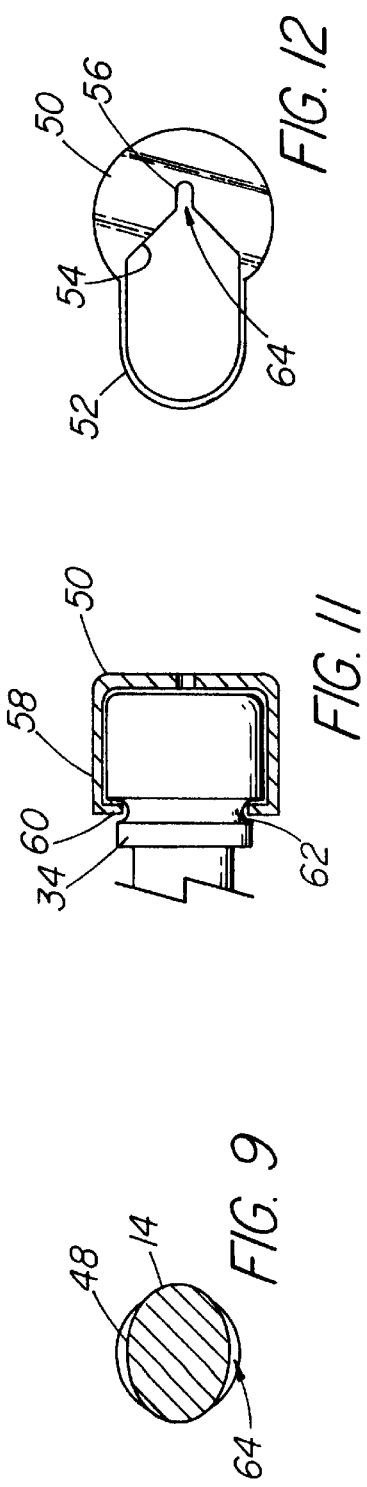

BRACHYTHERAPY DEVICE INCLUDING AN ANTI-STATIC HANDLE

CROSS-REFERENCE TO RELATED APPLICATIONS

This application claims priority of provisional application Ser. No. 60/093,469, filed Jul. 20, 1998.

TECHNICAL FIELD

This invention relates generally to medical devices and, in particular, to a brachytherapy device for exposing to radioactivity a human or veterinary patient.

BACKGROUND OF THE INVENTION

Brachytherapy is a known medical treatment for tumors and the like. More specifically, brachytherapy is a radiation treatment which entails the use of a solid or enclosed radioisotopic source positioned either on the surface of the body of the patient or at a short distance from the area to be treated. One form of brachytherapy is sometimes referred to as "interstitial" brachytherapy, in which radioactive implants are inserted into a tumor to be treated. Radioactivity from the implant shrinks the tumor or preferentially kills the cancerous cells making up the tumor, resulting in successful treatment of the patient. The present disclosure will use the word "brachytherapy" to refer to this latter form of treatment.

Brachytherapy typically involves the steps of positioning the end of a needle, cannula, catheter, or other elongate member or the like in or near the tumor; inserting a radioactive material into the needle, cannula, catheter or the like; allowing the radioactive material to remain near the tumor for a specific length of time; and removing the radioactive material and the needle, cannula, catheter, or other elongate member or the like after the treatment time has expired. In general, the order of the positioning and inserting steps is chosen as desired, depending upon the particular tumor being treated, the nature of the radioactive material and the characteristics of the needle, cannula, catheter, or elongate member or the like being used. Of course, access to the tumor can be established prior to the positioning and inserting steps via an introducer sheath or another needle, cannula, catheter or the like.

The radioactive material introduced during brachytherapy is often contained in a plurality of pellets or "seeds" which are inserted into an open end of the needle, cannula, catheter, or other elongate member and the like. Such seeds are sealed to prevent the leakage of the radioactive material from them. A stylet or other push rod is often used to advance the seeds to an appropriate position in the elongate member.

One commonly used seed comprises an iridium or iridium/platinum alloy core encased in a sheath of platinum. The iridium is irradiated to render it radioactive, in particular, to yield gamma-emitting $^{192}$Ir. A variety of other radioactive materials are known for this purpose, and are equally useful in brachytherapy. Typically, the radioactive seeds are 3 mm in length; during use, the individual seeds are separated by inert spacers of 7 mm length, so that there exists a known standard distance of one centimeter (1 cm) between the centers of the seeds. Knowledge of this distance is useful to the treating physician or surgeon for a variety of known reasons. The diameter of the radioactive seeds is selected as desired for the tumor to be treated, typically at or below about 0.040 in. (1.0 mm) diameter.

A number of practical problems have been encountered with existing apparatus for performing brachytherapy procedures. For example, it is often difficult to insert the radioactive seeds into the small diameter of the needle, cannula, catheter or the like. While it is known to orient such elongate members vertically as an aid to inserting the radioactive seeds, problems are still encountered due to the relatively small diameters employed, and due to the closeness of the diameters of the seeds (and spacers) and the interior diameters of the elongate members.

Moreover, the plastic materials often employed as handles for the elongate members are susceptible to generating an appreciable amount of static electricity. Such static electricity can cause the synthetic materials conventionally employed as spacers to cling to the handle ("static cling"), making it impossible to load the spacers into the elongate member through the handle. Such static electricity, when discharged, can also generate interference with some of the various sensing and other equipment present in the operating room. Finally, and perhaps most importantly, a static spark can be an ignition source in the presence of the oxygen and/or ether commonly employed within the operating room.

Another drawback to some brachytherapy devices (in particular, in those devices in which the elongate member is rigid) is the relative lack of control over the stylet or other push rod used to advance and position the radioactive seeds and the spacers. It is highly desirable that the stylet move with a minimal amount of force, since the radioactive seeds are often retained in the elongate member merely by a small (1 mm) wax plug in the distal end of the elongate member. Unfortunately, it has in fact been a common problem that the stylet is so loose within the rigid elongate member that the stylet readily falls outside the operating field, e.g., to the floor, if not carefully grasped. Since such a mishap can occur while the radioactive seeds are being inserted into the elongate member, too loose a stylet can increase patient and physician exposure to the seeds by what can be an appreciable amount. Too tight a fit between the stylet and elongate member is undesirable, however, because of the fine tactile feedback needed to sense when the seeds are completely inserted in the elongate member and abutted against the wax plug. A force sufficient to overcome undue friction can also unintentionally cause the stylet to eject the wax plug and radioactive seeds when such friction is overcome.

It would be highly advantageous to have a brachytherapy device which included a handle for the elongate member that facilitated the introduction of the radioactive seeds and the spacers into the elongate member. It would also be highly advantageous to have a brachytherapy device which included a handle that was anti-static or static electricity-free, or that was at least static electricity reduced by an amount to substantially eliminate (that is, eliminate to an extent desired for practical purposes) static interference, static cling and the risk of generating an ignition spark. Finally, it would further be highly advantageous to provide a controlled amount of friction between the elongate member and the stylet of a brachytherapy device, such that the stylet would not fall from the elongate member under weight of the stylet, yet also such that only a minimal amount of force was needed to overcome that friction, and such that such friction could be provided virtually the entire time any portion of the stylet was received in the elongate member.

SUMMARY OF THE INVENTION

The foregoing problems are solved and a technical advance is achieved in an illustrative brachytherapy device particularly adapted for exposing to radioactivity a human or veterinary patient. More particularly, the device of the present invention is directed to several improvements in brachytherapy devices. The present invention first involves employing a handle on the needle, cannula, catheter, or other elongate member and the like which is particularly configured for brachytherapy. The handle is anti-static, obviating the problems previously encountered with conventional needle handle materials. Additionally, or alternatively, the handle includes a specifically angled ramp surface which particularly facilitates the introduction of the radioactive seeds and the spacers into the elongate member, making brachytherapy procedures quicker and easier to perform. Finally, the device includes a portion near an end of either the elongate member or the stylet which provides a predetermined, local increase in friction between them, which prevents the stylet from falling out of the elongate member during use, yet which does not cause the stylet to bind in the elongate member and interfere with its easy smooth movement within the elongate member. All three of these improvements are included within the preferred embodiment of the invention.

The practical importance of solving these problems must not be overlooked. It is highly desirable during brachytherapy that both the patient and the healthcare staff be exposed to as little radiation as possible. Changes which shorten the time of exposure by even a few seconds can be important. The present invention speeds the introduction of the radioactive seeds into the elongate member, prevents the loss of time associated with replacing a stylet which has fallen outside the operating field, and avoids the risk of ignition associated with the use of ether as an anaesthetic. Taken together or separately, the improvements of the present invention represent a significant advance in brachytherapy procedures.

In a first aspect, then, the present invention is directed to a brachytherapy device for exposing to radioactivity a human or veterinary patient, comprising: an elongate member capable of containing radioactive material, the elongate member being adapted for introduction into the patient; and a handle at the proximal end of the elongate member, the handle being anti-static and being manipulable by a healthcare practitioner.

Preferably, the anti-static or reduced-static electricity material of the handle is at least incapable of generating a static spark under normal operating room conditions. More preferably, the material of the handle is incapable of generating a static spark even under unusual conditions, so that the material can properly be described as static-free, at least, for all practical purposes. As a brachytherapy device, the device of the present invention will likely be most commonly used for containing radioactive seeds (small pellets of an encapsulated radioactive material). Such seeds are spaced apart in the conventional manner by a plurality of inert spacers located one each between the individual seeds. It is preferred that the conductivity of the anti-static or reduced-static electricity material of the handle is sufficient to substantially preclude static cling of the spacers to the handle.

Suitable materials for the handle are expected to include polycarbonate resins, acrylic resins, acetal resins and hydroscopic nylon blends. It is preferred that the polycarbonate resins, the acrylic resins and the acetal resins be carbon-filled. Carbon-filled DELRIN® (a registered trademark of Du Pont, Wilmington, Del. USA, for its brand of thermoplastic acetal resin) and ZELUX CN® (a registered trademark of Westlake Plastics Company, Lanni, Pa. USA, for its brand of carbon powder-filled conductive polycarbonate resin) are two options that can be used. Electro Static Dissipative (ESD) poly carbonate from RTP Company, Winona, Minn., is particularly preferred in the practice of the present invention. Other polymeric materials, such as polyacetylene polymers, poly-p-phenylene polymers, poly(p-phenylene sulphide) polymers, polypyrrole polymers and poly-1,6-heptadiyne polymers, are believed to possess the requisite conductivity for use in the present invention. These other polymeric materials, however, can require modification to meet the mechanical requirements of the invention (resistance to sterilization techniques, mechanical strength, adhesion to the elongate member, and other practical requirements).

As indicated above, the brachytherapy device of this aspect of the present invention is preferably intended to be used with a plurality of radioactive seeds. More particularly, the device is preferably adapted to allow the introduction of the radioactive seeds into the elongate member through the handle and the subsequent containment of the seeds in the elongate member. The spacers are similarly introduced and contained in the elongate member, located between individual ones of the plurality of seeds.

The brachytherapy device of this first aspect of the present invention preferably includes an elongate member which is hollow, configured, for example, as a needle or cannula. The device of this aspect of the present invention preferably further comprises a stylet slideably received in the elongate member. More specifically, the elongate member preferably includes a longitudinal throughbore therein, and the handle connected to the elongate member includes an interior ramp surface therein in communication with the longitudinal throughbore of the elongate member. The interior ramp surface of the handle is preferably frustoconical in shape and possesses an included apical angle of at least about 16°, and more preferably about 24°. Additional surfaces leading into the ramp surface are of course contemplated within the present invention, but are probably not preferred, while an additional bore surface in the handle leading away from the ramp surface and to the elongate member is convenient and is described in more detail below.

In a second aspect, the present invention is directed to a brachytherapy device for exposing to radioactivity a human or veterinary patient, comprising: an elongate member capable of containing a radioactive material, the elongate member being adapted for introduction into the patient, and the elongate member including a longitudinal throughbore therein and a proximal end; a stylet slideably receivable in the longitudinal throughbore of the elongate member, the stylet including a distal end; and a portion near at least one of the proximal ends of the elongate member and the distal end of the stylet, the portion providing a local, defined amount of friction between the elongate member and the stylet; wherein the stylet is otherwise generally closely dimensioned to the longitudinal throughbore in the elongate member such that the stylet would be generally freely movable in the throughbore in the absence of the portion. Preferably, the local, defined amount of friction provided by the portion is just adequate to prevent sliding of the stylet in the throughbore of the elongate member under weight of the stylet.

In this second aspect, the brachytherapy device of the present invention preferably includes the handle disclosed above. Also preferably, the elongate member is configured as a needle or a cannula. Further, in this and the other aspects of the present invention, the entire insertable length of the stylet is equal to or just slightly less than the overall length of the elongate member and connected handle, so that the stylet can be used to eject the contained radioactive material and the inert seeds from the elongate member during and/or after treatment of the patient.

The portion providing the localized friction can be formed in a variety of ways. For example, the portion can comprise a crimp in the elongate member. Alternatively, the portion can comprise an elliptical or oval deformation of the elongate member. The portion providing localized friction can instead comprise a cap near the proximal end of the elongate member. The cap preferably includes a V-shaped notch and a recess in the notch, the recess being dimensioned to receive the distal end of the stylet therethrough, and the notch being dimensioned to allow access through it to the throughbore in the elongate member. Finally, the portion can be formed as a projection (such as an annular ring or an evenly spaced plurality of projections) inside the handle itself, preferably located distal of the ramp surface (for example, on the additional bore surface). In each of these cases, of course, the portion providing localized friction will still be near the proximal end of the elongate member.

When the portion is instead near the distal end of the stylet, the portion can comprise a crimp or flange on the stylet. This is probably the easiest way to form the portion.

The size of the portion need not be very large to achieve the goals of this aspect of the present invention. Indeed, in devices employing needles and stylets of the sizes indicated below, the portion providing localized friction can be barely visible to the unaided eye. Accordingly, the accompanying drawing should be considered as showing the portion in exaggerated scale, in comparison to the balance of the embodiments disclosed in the drawing. In particular, the device of the present invention is preferably employed with the radioactive seeds and the spacers mentioned above. It is highly desirable that there be no way for the seeds and spacers to become trapped unintentionally within the elongate member after use. (During use, of course, the seeds and spacers are retained within the throughbore of the elongate member in any convenient way, for example, by a small plug of wax closing the distal end of the throughbore. In another preferred treatment, the seeds and retainers are ejected from the elongate member and implanted in the patient at the treatment site.) Therefore, the portion preferably possesses a minimum transverse extent in any direction which is greater than the smallest transverse dimension of the radioactive seeds and the spacers.

It is important to note in regard to this aspect of the present invention that a simple bend, curve or kink in either the elongate member or the stylet is likely to be unacceptable in providing a predetermined and localized amount of friction between them. Even a relatively small kink would likely provide far too much friction, and would be expected to require an unacceptable amount of force to achieve relative movement of the stylet and elongate member. A bend or curve would cause the stylet to rub against the elongate member at two or more moving locations; the resulting frictional resistance to movement would therefore be expected to disadvantageously vary in dependence upon the length of the particular segment of the stylet which happened to lie within the elongate member at one time or another during use.

In a third aspect, the present invention is directed to a brachytherapy device for exposing to radioactivity a human or veterinary patient, comprising: an elongate member capable of containing a radioactive material, the elongate member being adapted for introduction into the patient, and the elongate member including a longitudinal throughbore therein and a proximal end; a stylet slideably receivable in the longitudinal throughbore of the elongate member, the stylet including a distal end; a portion near at least one of the proximal end of the elongate member and the distal end of the stylet, the portion providing a local, defined amount of friction between the elongate member and the stylet; and a handle connected to the elongate member, wherein the handle includes an interior ramp surface therein in communication with the longitudinal throughbore of the elongate member; wherein the interior ramp surface of the handle is frustoconical in shape and possesses an included apical angle of at least about 16°; and wherein the handle is anti-static and is manipulable by a healthcare practitioner; wherein the elongate member comprises a needle or cannula; wherein the portion comprises a crimp or flange on the stylet; wherein the local, defined amount of friction provided by the portion is just adequate to prevent sliding of the stylet in the throughbore of the elongate member under weight of the stylet; wherein the anti-static handle is incapable of generating a static spark under normal operating room conditions; wherein the anti-static handle comprises an ESD carbon-filled polycarbonate resin, a carbon-filled acrylic resin, a carbon-filled acetal resin or a hydroscopic nylon blend or otherwise electro static reduced polymer; and wherein the stylet is otherwise generally closely dimensioned to the longitudinal throughbore in the elongate member such that the stylet would be generally freely movable in the throughbore in the absence of the portion.

The medical device of the present invention possesses significant advantages over prior brachytherapy devices. The preferred ramp surface in the handle facilitates the insertion of the radioactive seeds and the spacers into the elongate member. The preferred anti-static handle eliminates, for practical purposes, the previously encountered risks of static interference, static cling and ignition spark generation. Finally, the localized friction portion provides a controlled and predetermined amount of friction between the elongate member and the stylet of a brachytherapy device, preventing the stylet from falling from the elongate member, while also preventing or reducing the risk of unintended ejection of the radioactive seeds and inert spacers from the elongate member. Such friction is provided virtually the entire time any portion of the stylet is received in the elongate member.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a side view of a first preferred embodiment of the present invention;

FIG. 2 is a cross-sectional view taken along line of 2—2 FIG. 1;

FIG. 3 is a cross-sectional view taken along line 3—3 of FIG. 2;

FIG. 4 is an enlarged view of a portion of the view shown in FIG. 2;

FIG. 5 is a cross-sectional view taken along line 5—5 of FIG. 4;

FIG. 6 is a cross-sectional view of another preferred embodiment of the present invention, similar to FIG. 5;

FIG. 7 is a top view of a portion of another preferred embodiment of the present invention;

FIG. 8 is a side view of the portion of the invention shown in FIG. 7;

FIG. 9 is a cross-sectional view taken along line 9—9 of FIG. 8;

FIG. 11 is a partial cross-sectional view of a portion of another preferred embodiment of the present invention; and FIG. 12 is a right hand (top) view of the portion of the invention shown in FIG. 11.

DETAILED DESCRIPTION

Figure 10:
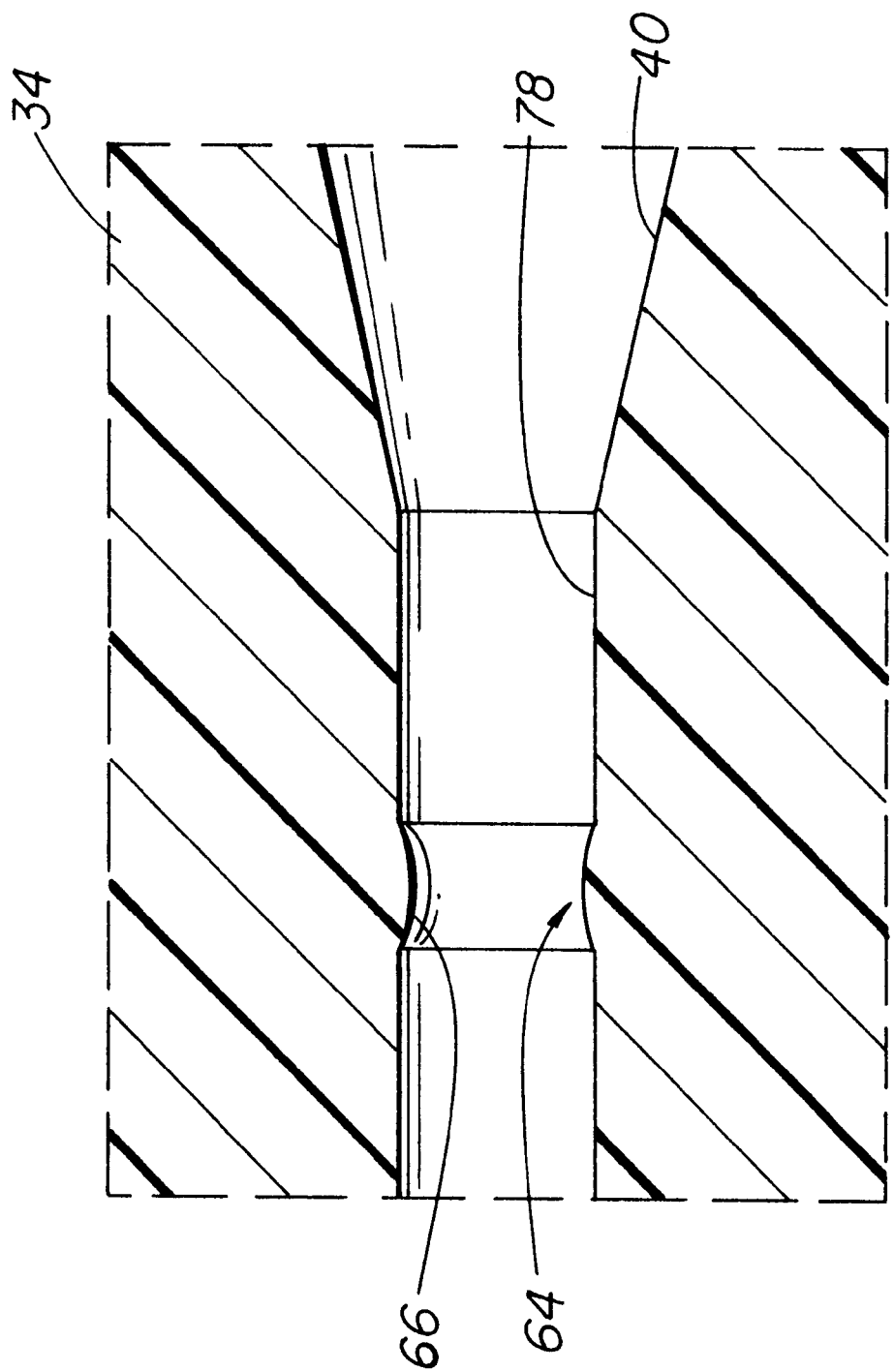
FIG. 10 is a cross-sectional view of a portion of another preferred embodiment of the present invention, comparable to FIG. 2.

With reference first to FIG. 1, a first embodiment of a brachytherapy device 10 according to the present invention is thereshown, useful for exposing to radioactivity a human or veterinary patient. The brachytherapy device 10 first comprises an elongate member 12 capable of containing a radioactive material, the elongate member 12 being adapted for introduction into the patient. As mentioned above, the elongate member 12 can be either flexible (such as a catheter) or rigid (such as a needle or cannula), depending upon the particular tumor being treated and the particular radioactive material being employed. Preferably, the elongate member 12 is rigid and composed of a suitable medical grade material, such as stainless steel. More preferably, the elongate member 12 is configured as a rigid tubular member such as a needle or cannula, most preferably as a needle. Accordingly, while the elongate member 12 can sometimes be referred to herein as the needle 12, it should be understood that the elongate member 12 need not necessarily be a needle.

The needle or other elongate member 12 preferably includes a longitudinal throughbore 16 therein, extending from the proximal end 18 of the needle 12 to the distal end 20 of the needle 12. The inner and outer diameters of the needle or other elongate member 12 (the former diameter serving as the diameter of the throughbore 16) are selected in dependence upon the particular tumor being treated, the route of access to the tumor and the configuration of the radioactive material to be inserted in it. The embodiments of the brachytherapy device 10 disclosed herein are generally useful with either small radioactive seeds or larger radioactive seeds, as large as about 0.040 in. (about 1.0 mm) in diameter and several millimeters (for example, 3 mm as is conventional) in length. Thus, a convenient inner diameter for the needle 12 is about 0.041 to 0.042 in. (1.04 to 1.07 mm), while a convenient outer diameter for the needle 12 is about 0.053±0.001 in. (1.35±0.03 mm).

The needle 12 conveniently includes a sharp, beveled tip 68 at its distal end 20. For further convenience, although omitted from FIG. 1, the needle 12 might bear on it a plurality of etched markings spaced 1 cm apart; these would allow the position of the device 10 with respect to the tumor to be judged with fair precision. Preferably, however, for better judging the position of the distal end 20 of the needle 12, the needle 12 bears on its distal end 20 some dimpling 70 which serves to permit the position of the distal end 20 to be determined even more precisely by ultrasound or echo location. Most preferably, the dimpling 70 is ECHOGENIC™-brand dimpling (ECHOGENIC™ is a trademark of Cook Incorporated, Bloomington, Ind. USA).

As also shown in FIG. 1, this first preferred embodiment of the brachytherapy device 10 of the present invention also comprises a stylet 14 or other push rod slideably receivable in the longitudinal throughbore 16 of the needle or other elongate member 12. The stylet 14 includes a proximal end 22 carrying on it a stylet knob 72, and a distal end 24 opposite the proximal end 22. A plurality of etched markings 32 are positioned on the stylet 14 near its proximal end 22, for allowing the relative position of the distal end 24 of the stylet 14 with respect to the distal end 20 of the needle 12 to be judged with good precision. The markings 32 are spaced 1 cm apart.

With continued reference to FIG. 1, but with reference also being had to FIG. 2, the brachytherapy device 10 of the present invention next comprises a handle or hub 34 connected to the needle or other elongate member 12, for example, at the proximal end 18 of the needle 12. Such connection is made in any convenient manner. Preferably, the handle 34 includes a recess 38 receiving part of the distal end 18 of the needle 12 therein. The handle 34 is retained on the needle 12 by an adhesive 38 positioned in the recess 36. The handle 34 also preferably includes a tapered ramp surface 40 opposite the recess 38, extending into and partway through the handle 34 in communication with the longitudinal throughbore of the needle 12. The handle 34 preferably further includes an additional bore surface 78 extending between the ramp surface 40 and the recess 36 (and thereby the proximal end 18 of the needle 12) for achieving such communication. The transverse diameter of the bore surface 78 is preferably the same as the interior diameter of the needle 12.

To permit proper positioning of the distal end 20 of the needle 12 with respect to the tumor to be treated, the handle 34 of the of the needle 12 is adapted for manipulation by a healthcare practitioner, for example, the operating physician or surgeon. To assist such manipulation, as shown in FIGS. 2 and 3, the handle 34 preferably includes an outwardly extending flange 74 and a tactile post 76 on the flange 74.

The brachytherapy device 10 of the present invention is preferably used in conjunction with a plurality of radioactive seeds and inert spacers of conventional type. Only a single conventional platinum-encased $^{192}$Ir-platinum alloy radioactive seed 26 is shown in FIG. 1, along with a single inert spacer 28 composed, for example, of suture material. Other radioactive seeds 26 or other radioactive material configurations can of course be used as well. The particular radioactive material used in the seeds 26 and/or the number of seeds 26 is selected in dependence upon the size of the tumor to be treated and the dose of radioactivity to which the patient is to be subjected. Preferably, the individual seeds 26 are each separated by one of the spacers 28. Also preferably, in the conventional manner the individual seeds are 3 mm in length, while the spacers are 7 mm in length; this provides a standard 1 cm between seed centers when inserted in the needle or other elongate member 12.

Conveniently, the needle or other elongate member 12 and its attached handle 34 are oriented vertically during insertion of the radioactive seeds 26 and inert spacers 28 into the throughbore 16 of the needle 12. A 1 mm wax plug 30 in the distal end 20 of the needle (shown in phantom in FIG. 1), closely adjacent the sharp tip 68 of the needle 12, prevents the seeds 26 and spacers 28 from falling out the distal end 20 of the needle 12.

The ramp surface 40 in the handle 34 is particularly adapted to assist insertion of the seeds 26 and spacers 28. In particular, the ramp surface 40 is preferably frustoconical (a truncated cone) in shape, and preferably possesses an included apical (apex) angle of at least about 16°. The "included" angle refers to the complete angle swept by the ramp surface 40, not the angle the ramp surface 40 makes with respect to its axis. As shown in FIG. 2, the included apical angle of the frustoconical ramp surface 40 is most preferably about 24°. An included apical angle of at least 16° not only facilitates engagement of the seeds 26 and spacers 28 with the additional bore surface 78 in the handle 34, it also facilitates engagement of the distal end 24 of the stylet 14 with the seeds 26 and spacers 28 to allow their proper and complete positioning in, and proper advancement through, the bore defined by the bore surface 78 and the interior of the needle 12.

It should be evident that this is the second aspect of the present invention mentioned above. It should also be evident that a change in the taper of the ramp surface 40, or the inclusion of an additional surface portion, proximal of the ramp surface 40 but having a shape different from that of the ramp surface 40, is not precluded. An additional surface portion of different shape (that is, other than frustoconical) is not preferred, however. If such a different shaped surface is present, it should have a larger diameter than the proximal diameter of the ramp surface 40.

With regard to the first aspect of the present invention mentioned above, the handle 34 is preferably composed of an anti-static, a static electricity-free, or a reduced-static electricity material. For practical purposes, the three phrases should be considered to have the same meaning: the material of the handle 34 is sufficiently conductive to be incapable of, and is otherwise incapable of, generating a static spark under normal operating room conditions. Because of variations in operating room temperature, humidity, and presence or absence of other sources of static charge, a more quantitative definition of these phrases may not really be possible. However, those of even rudimentary skill in this art are well aware of the problems associated with static electricity in the operating room, and should be well capable of recognizing when static electricity has been eliminated, at least as a practical concern. It is preferred that the conductivity of the handle 34 be sufficient to preclude or substantially preclude static cling of the inert spacers 28 to the handle 34. This, too, is a matter of practical consequence, rather than a matter of precise numerical limits.

By way of example, however, several materials can be noted as being useful or as being expected to be useful for an anti-static, a reduced-static, or static-free handle 34. Preferably, the reduced-static electricity material of the handle 34 comprises a polycarbonate resin, an acrylic resin, an acetal resin or a hydroscopic nylon blend. If used, the polycarbonate resin, the acrylic resin or the acetal resin is preferably carbon-filled. Carbon-filled DELRIN® (a registered trademark of Du Pont, Wilmington, Del. USA, for its brand of thermoplastic acetal resin) and ZELUX CN® (a registered trademark of Westlake Plastics Company, Lanni, Pa. USA, for its brand of carbon powder-filled conductive polycarbonate resin) are two options that can be used. Electro Static Dissipative (ESD) poly carbonate from RTP Company, Winona, Minn., is particularly preferred in the practice of the present invention. (Such materials are also useful for the knob 72 of the stylet 14.) Other polymeric materials, such as polyacetylene polymers, poly-p-phenylene polymers, poly(p-phenylene sulphide) polymers, polypyrrole polymers and poly-1,6-heptadiyne polymers, are believed to possess the requisite conductivity for use in the present invention. However, these other polymeric materials can require modification to meet the mechanical requirements of the invention (resistance to sterilization techniques, mechanical strength, adhesion to the elongate member, and other practical requirements).

With regard to another aspect of the present invention, the brachytherapy device 10 of the present invention further preferably comprises a portion 64 located near either the proximal end 18 of the needle or other elongate member 12, or the distal end 24 of the stylet 14, which provides a local, defined amount of friction between the elongate member 12 and the stylet 14. The former of these locations is shown in FIGS. 4 through 6 and FIGS. 10 through 12, while the latter of these locations is shown in FIGS. 7 through 9. The stylet 14 is otherwise generally closely dimensioned to the throughbore 16 of the needle 12, such that the stylet 14 would be generally freely movable in the throughbore 16 in the absence of the portion 64. For example, when the inside diameter of the needle 12 is in the range mentioned above, that is, about 0.041 to 0.042 in. (1.04 to 1.07 mm), the stylet 14 can have a diameter of about 0.038 in. (0.97 mm).

When positioned near the proximal end 18 of the needle or other elongate member 12, the portion 64 can comprise a crimp 44 (FIGS. 4 and 5) in the needle 12, an elliptical or oval deformation 46 of the needle 12 (FIG. 6), or even an annular projection 66 on the bore surface 78 in the handle 34 (FIG. 10). Alternatively, the portion can comprise a cap 50 carried on the handle 34 which partially covers the ramp surface 40. (The annular projection 66 and the cap 50 are still positioned near the proximal end 18 of the needle 12, even if not actually positioned on the needle 12 itself.) The cap 50 preferably includes a wall 58 from which a flange 60 extends inwardly and engages a groove 62 on the handle 34. The cap 50 also preferably includes a V-shaped notch 54 and a small, semicircular recess 56 in the apex of the notch 54. The recess 56 is dimensioned to receive the distal end 24 of the stylet 14 therethrough and provide localized friction against the stylet 14, while the notch 54 is dimensioned to allow access therethrough to the throughbore 16 in the needle 12 (via the ramp surface 40), each when the flange 60 is engaged with the groove 62. The cap 50 can further include a retaining ring 52 which engages the groove 62 when the flange 60 does not, keeping the cap 50 associated with the handle 34 and needle 12 even when not in use.

More preferably, however, the portion 64 is instead positioned near the distal end 24 of the stylet 14. When so positioned, the portion 64 can comprise a crimp or flange 48 on the stylet 14 (FIGS. 7 through 9), or some other alteration in the uniformity of the diameter or circumference of the distal end 24 of the stylet 14. Such a crimp or flange 48 is probably the simplest way to form the portion 64. Preferably, the crimp or flange 48 is located about 1 cm proximal of the distal extremity of the distal end 24 of the stylet 14.

The application of localized friction near either of these two locations, that is, near the proximal end 18 of the needle 12 or near the distal end 24 of the stylet 14, has the particular advantage that the engagement of the stylet 14 in the throughbore 16 of the needle 12 is subject to a controlled amount of friction through most or almost all of the time of such engagement. Other locations would provide an appreciable length of engagement during which such friction was absent.

The transverse deformation of the portion 64 is shown exaggerated to some degree in the Figures; the actual amount of deformation is preferably adequate to provide a local, predetermined and defined amount of friction just adequate to prevent sliding of the stylet 14 in the throughbore 16 of the needle or other elongate member 12 under weight of the stylet 14. Moreover, it is important that the portion 64 not interfere with the insertion or removal of the radioactive seeds 26 and inert spacers 28 from the needle 12. Accordingly, the portion 64 should possess a minimum transverse extent which is greater than the largest transverse dimension of the seeds 26 and the spacers 28.

A quantitative example should suffice. The crimp or flange 48 on the stylet 14 can be about 0.035 in. by about 0.040 in. (0.89 mm by 1.02 mm) when the stylet is about 0.037 to 0.039 in. (0.94 to 0.99 mm) in diameter. Thus, the minimum transverse width of the crimp or flange 48 in the view shown in FIG. 7 (and FIG. 9) is about 0.035 to 0.036 in. (0.89 to 0.91 mm), while the maximum transverse width of the crimp or flange 48 in the view shown in FIG. 8 (and FIG. 9) is about 0.039 to 0.040 in. (0.99 mm to 1.02 mm). The portion 64 should be sized similarly when positioned near the proximal end 18 of the needle 12, rather than near the distal end 24 of the stylet 14.

The overall lengths of the needle or other elongate member 12, of the handle 34 and of the stylet 14 are selected in dependence upon the site of the particular tumor to be treated. Conveniently, a typical embodiment of the brachytherapy device 10 of the present invention can have a handle 34 which is about 1.21 in. (3.07 cm) in overall length, a needle 12 which is about 20.0 cm ±0.1 cm in overall length, and a stylet 14 which is about 23.0 cm–0.1 cm, +0.0 cm, in overall length. However, it is contemplated that the needle can range in length from 5 to 50 cm depending on the particular treatment and anatomical site. What is more important than these precise lengths, however, the relative length of the stylet 14, the needle 12 and the handle 34 when fully engaged. More particularly, it is highly desirable that the length of the stylet 14 be such that, when the stylet 14 is fully received in the needle 12 and the knob 72 abuts the handle 34, the proximal end 24 of the stylet 14 is just exposed through the sharp tip 68 of the needle 12, or extends perhaps a millimeter or so through it. This ensures that when the stylet 14 is advanced to this position all of the radioactive seeds 26 and inert spacers 28 are ejected from the needle 12.

It should be clear that the present invention thus provides a brachytherapy device 10 which possesses significant advantages over prior devices for that purpose. The preferred ramp surface 40 in the handle 34 facilitates the insertion of the radioactive seeds 26 and the spacers 28 into the needle or other elongate member 12. The preferred anti-static, reduced-static, or static-free handle 34 eliminates, for practical purposes, the previously encountered risks of static interference, static cling and ignition spark generation. Finally, the localized friction portion 64 near the proximal end 18 of the needle 12 or the distal end 24 of the stylet 14 provides a controlled and predetermined amount of friction between the needle 12 and the stylet 14 of the brachytherapy device 10, preventing the stylet 14 from falling from the needle, while also preventing or reducing the risk of unintended ejection of the radioactive seeds 28 and inert spacers 26 from the needle 12. Such friction is advantageously provided virtually the entire time any portion of the stylet 14 is received in the needle 12.

The details of the construction or composition of the various elements of the brachytherapy device 10 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure.

Industrial Applicability

The present invention is useful for the introduction of a contained radioactive material during brachytherapy, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A brachytherapy device (10) for exposing radioactivity to a human or veterinary patient, comprising:
   an elongate member (12) capable of containing radioactive material, the elongate member (12) being adapted for introduction into the patient; and
   a handle (34) at the proximal end of the elongate member (12), the handle (34) being anti-static and being manipulable by a healthcare practitioner.

2. The device (10) according to claim 1, wherein the handle (34) comprises a polycarbonate resin, an acrylic resin, an acetal resin, a hydroscopic nylon blend, a polyacetylene polymer, a poly-p-phenylene polymer, a poly(p-phenylene sulphide)polymer, a polypyrrole polymer or a poly-1,6-heptadiyne polymer.

3. The device (10) according to claim 2, wherein the polycarbonate resin, the acrylic resin or the acetal resin is carbon-filled.

4. The device (10) according to claim 1, wherein the device (10) is adapted for use with a plurality of radioactive seeds (26) introduced into the elongate member (12) through the handle (34) and contained in the elongate member (12), and at least one spacer (28) similarly introduced and contained in the elongate member (12), located between individual ones of the plurality of seeds (26); wherein the conductivity of the handle (34) is sufficient to substantially preclude static cling of the at least one spacer (28) to the handle (34).

5. The device (10) according to claim 1, wherein the elongate member (12) is hollow, and wherein the device (10) further comprises a stylet (14) slideably received in the elongate member (12).

6. The device (10) according to claim 5, wherein the elongate member (12) includes a longitudinal throughbore (16) therein, and wherein the handle (34) includes an interior ramp surface (40) therein in communication with the longitudinal throughbore (16) of the elongate member (12).

7. The device (10) according to claim 6, wherein the interior ramp surface (40) of the handle (34) is frustoconical in shape and possesses an included apical angle of at least about 16°.

8. The device (10) according to claim 7, wherein the included apical angle of the interior ramp surface (40) of the handle (34) is about 24°.

9. A brachytherapy device (10) for exposing radioactivity to a human or veterinary patient, comprising:
   an elongate member (12) capable of containing a radioactive material, the elongate member (12) being adapted for introduction into the patient, and the elongate member (12) including a longitudinal throughbore (16) therein and a proximal end (18);
   a stylet (14) slideably receivable in the longitudinal throughbore (16) of the elongate member (12), the stylet (14) including a distal end (24); and
   a portion (64) near at least one of the proximal end (18) of the elongate member (12) and the distal end (24) of the stylet (14), the portion (64) providing a local, defined amount of friction between the elongate member (12) and the stylet (14);

wherein the stylet (14) is otherwise generally closely dimensioned to the longitudinal throughbore (16) in the elongate member (12) such that the stylet (14) would be generally freely movable in the throughbore (16) in the absence of the portion (64).

10. The device (10) according to claim 9, wherein the portion (64) comprises a crimp (44) in the elongate member (12).

11. The device (10) according to claim 9, wherein the portion (64) comprises an elliptical or oval deformation (46) of the elongate member (12).

12. The device (10) according to claim 9, wherein the portion (64) comprises at least one of a crimp and a flange (48) on the stylet (14).

13. The device (10) according to claim 9, wherein the local, defined amount of friction provided by the portion (64) is just adequate to prevent sliding of the stylet (14) in the throughbore (16) of the elongate member (12) under weight of the stylet (14).

14. The device (10) according to claim 9, wherein the portion (64) comprises a cap (50) near the proximal end (18) of the elongate member (12).

15. The device (10) according to claim 14, wherein the cap (50) includes a V-shaped notch (54) and a recess (56) in the notch (54), the recess (56) being dimensioned to receive the distal end (24) of the stylet (14) therethrough, and the notch (54) being dimensioned to allow access therethrough to the throughbore (16) in the elongate member (12).

16. The device (10) according to claim 9, further comprising a handle (34) connected to the elongate member (12), the handle (34) being manipulable by a healthcare practitioner; wherein the handle (34) includes an interior ramp surface (40) therein in communication with the longitudinal throughbore (16) of the elongate member (12); and wherein the interior ramp surface (40) of the handle (34) is frustoconical in shape and possesses an included apical angle of at least about 16°.

17. The device (10) according to claim 9, further comprising a handle (34) connected to the elongate member (12), the handle (34) being anti-static and being manipulable by a healthcare practitioner.

18. The device (10) according to claim 17, wherein the handle (34) comprises a polycarbonate resin, an acrylic resin, an acetal resin, a hydroscopic nylon blend, a polyacetylene polymer, a poly-p-phenylene polymer, a poly(p-phenylene sulphide) polymer, a polypyrrole polymer or a poly-1,6-heptadiyne polymer.

19. The device (10) according to claim 9, wherein the device (10) is adapted for use with a plurality of radioactive seeds (26) introduced into the elongate member (12) through the handle (34) and contained in the elongate member (12), and at least one spacer (28) similarly introduced and contained in the elongate member (12), located between individual ones of the plurality of seeds (26); wherein the conductivity of the handle (34) is sufficient to substantially preclude static cling of the at least one spacer (28) to the handle (34).

20. A brachytherapy device (10) for exposing radioactivity to a human or veterinary patient, comprising:

an elongate member (12) capable of containing a radioactive material, the elongate member (12) being adapted for introduction into the patient, and the elongate member (12) including a longitudinal throughbore (16) therein and a proximal end (18);

a stylet (14) slideably receivable in the longitudinal throughbore (16) of the elongate member (12), the stylet (14) including a distal end (24);

a portion (64) near at least one of the proximal end (18) of the elongate member (12) and the distal end (24) of the stylet (14), the portion (64) providing a local, defined amount of friction between the elongate member (12) and the stylet (14); and a handle (34) connected to the elongate member (12), wherein the handle (34) includes an interior ramp surface (40) therein in communication with the longitudinal throughbore (16) of the elongate member (12); wherein the interior ramp surface (40) of the handle (34) is frustoconical in shape and possesses an included apical angle of at least about 16°; and wherein the handle (34) is anti-static and is manipulable by a healthcare practitioner;

wherein the elongate member (12) comprises a needle or cannula (12);

wherein the portion (64) comprises at least one of a crimp or a flange (48) on the stylet (14);

wherein the local, defined amount of friction provided by the portion (64) is just adequate to prevent sliding of the stylet (14) in the throughbore (16) of the elongate member (12) under weight of the stylet (14);

wherein the handle (34) is incapable of generating a static spark under normal operating room conditions;

wherein the handle (34) comprises a carbon-filled polycarbonate resin, a carbon-filled acrylic resin, a carbon-filled acetal resin or a hydroscopic nylon blend or otherwise electro static reduced polymer; and wherein the stylet (14) is otherwise generally closely dimensioned to the longitudinal throughbore (16) in the elongate member (12) such that the stylet (14) would be generally freely movable in the throughbore (16) in the absence of the portion (64).

* * * * *